(12) United States Patent
Chen et al.

(10) Patent No.: US 6,948,354 B1
(45) Date of Patent: Sep. 27, 2005

(54) WATER RESISTANT, VENTILATORY EXAMINING DEVICE FOR CLOTH

(75) Inventors: Jason Chen, Sinjhuang (TW); Stephen Li, Taichung (TW); Jimmy Lay, Sinjhuang (TW); Murphy Tsorng, Yonghe (TW)

(73) Assignee: Singtex Industrial Co., Ltd., Taipei Hsien (TW)

( * ) Notice: Subject to any disclaimer, the term of this patent is extended or adjusted under 35 U.S.C. 154(b) by 29 days.

(21) Appl. No.: 10/807,108

(22) Filed: Mar. 24, 2004

(51) Int. Cl.[7] ............................................. G01N 15/08
(52) U.S. Cl. ........................................................... 73/38
(58) Field of Search ........................... 73/38; 403/278, 403/305

(56) References Cited

U.S. PATENT DOCUMENTS

| | | | |
|---|---|---|---|
| 669,529 A * | 3/1901 | Kennedy ........................ | 73/38 |
| 3,116,629 A * | 1/1964 | Gross ............................ | 73/38 |
| 3,521,913 A * | 7/1970 | Verhein et al. ............. | 285/109 |
| 4,194,041 A * | 3/1980 | Gore et al. ................. | 442/289 |
| 4,581,921 A * | 4/1986 | Gillespie et al. ............... | 73/73 |
| 4,846,970 A * | 7/1989 | Bertelsen et al. ........... | 210/232 |
| 5,887,477 A * | 3/1999 | Newman ...................... | 73/159 |
| 6,032,515 A * | 3/2000 | Huber ........................ | 73/49.1 |
| 6,119,506 A * | 9/2000 | Gibson et al. ................. | 73/38 |
| 6,196,055 B1 * | 3/2001 | Haines ......................... | 73/38 |
| 6,360,588 B1 * | 3/2002 | Ross et al. .................... | 73/38 |
| 6,655,192 B2 * | 12/2003 | Chavdar ....................... | 73/38 |

* cited by examiner

Primary Examiner—Hezron Williams
Assistant Examiner—John Fitzgerald
(74) Attorney, Agent, or Firm—Rosenberg, Klein & Lee

(57) ABSTRACT

An examining device for cloth includes a first container having two opposite open ends, a second container having a closed end and an open end, a combining device to combine the first container and the second container and an air supply device in connection with the second container to supply air into the second container. After a cloth is sandwiched between the combining means and the first container and after the first container is filled with water and the second container is supplied with air, observation made to see if water seeps through the cloth and air passes through the cloth is able to test capabilities of the cloth.

8 Claims, 7 Drawing Sheets

WATER RESISTANT, VENTILATORY EXAMINING DEVICE FOR CLOTH

BACKGROUND OF THE INVENTION

1. Field of the Invention

The present invention relates to an examining device, and more particularly to a water resistant and ventilatory examining device for cloth to see if the cloth produced is able to resist water penetration and is air-permeable.

2. Description of Related Art

Nowadays, cloth made for clothes has meshes smaller than a water molecule and larger than an air molecule so that the cloth is able to resist water penetration and still allow air to penetrate. Thus, when a user is wearing clothes made of the specially produced cloth, the rain drops will not penetrate the cloth and the user is able to keep dry during a rainy day. In the meantime, the moisture perspired by the user is able to penetrate the cloth and the user is able to feel comfortable even after a large amount of perspiration.

In order to test whether the cloth so produced has the desired function, different and expensive machinery is introduced to the market. Although they do meet the requirements and successfully test the cloth, complex steps and large manual effort are involved, which hinders the popularity of the existing testing devices.

To overcome the shortcomings, the present invention tends to provide an improved examining device to mitigate the aforementioned problems.

SUMMARY OF THE INVENTION

The primary objective of the present invention is to provide an improved water resistant and ventilatory examining device for cloth. The examining device is simple in structure and low in cost.

Other objects, advantages and novel features of the invention will become more apparent from the following detailed description when taken in conjunction with the accompanying drawings.

DETAILED DESCRIPTION OF THE PREFERRED EMBODIMENT

Figure 1:
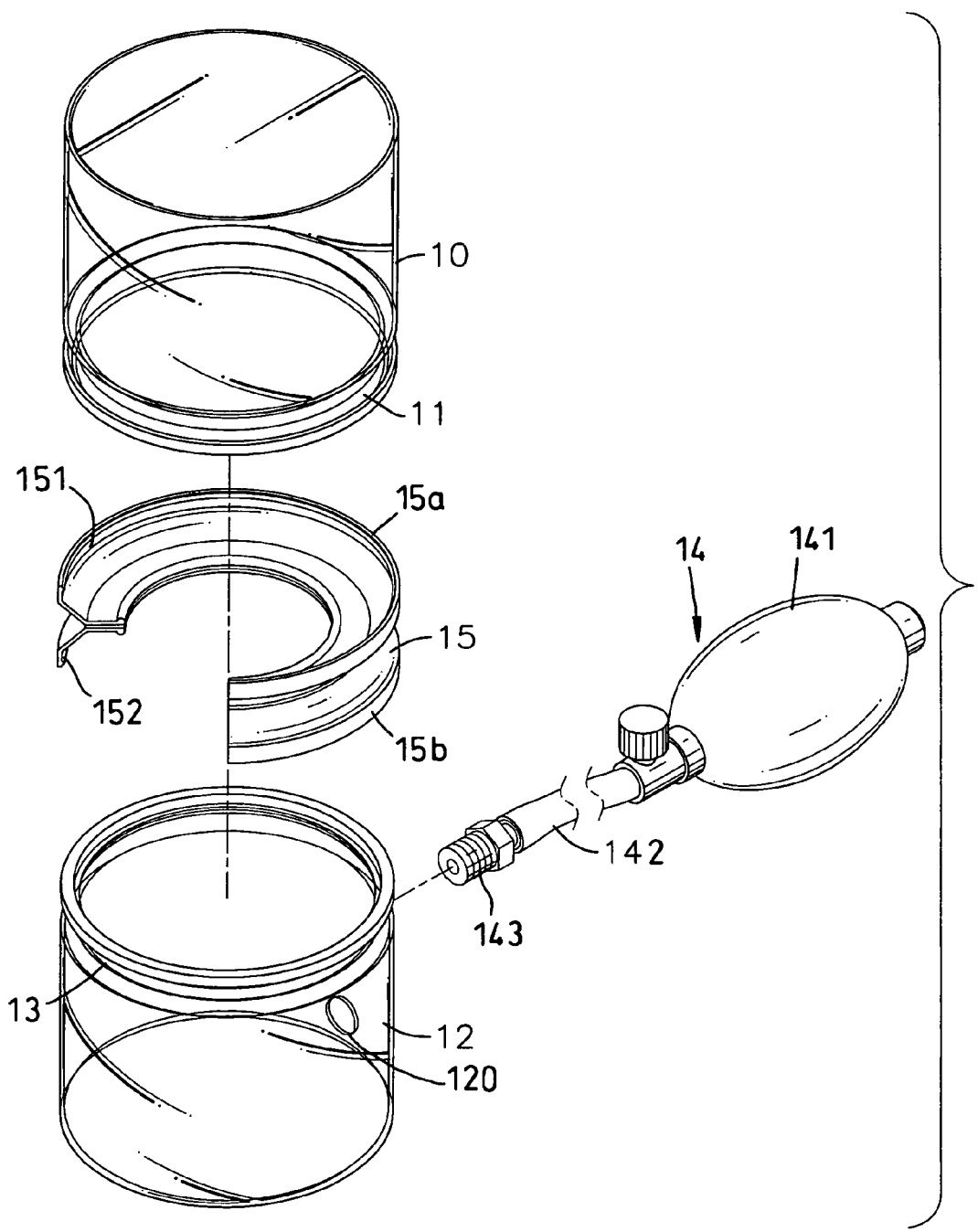
FIG. 1 is an exploded perspective view of the examining device of the present invention.

With reference to FIG. 1, the water resistant and ventilatory examining device for cloth includes a first container (10), a second container (12), a connector (15) sandwiched between the first container (10) and the second container (12) and an air supply device (14).

The first container (10) has a bottom open end defined in a bottom end of the first container (10) and a top open end defined in a top end of the first container (10). A first annular groove (11) is defined in an outer periphery adjacent to the open end.

The second container (12) has an open end defined in a top end of the second container (12) and a closed end defined in a bottom end of the second container (12). A second annular groove (13) is defined in an outer periphery adjacent to the open end of the second container (12). An air hole (120) is defined through a side wall of the second container (12) to allow the surrounding air to communicate with the inside of the second container (12).

The air supply device (14) has an air bulb (141) and a tube (142) extending from the air bulb (141) and having a nozzle (143) formed on a free end of the tube (142) to correspond to the air hole (120) of the second container (12).

Figure 2:
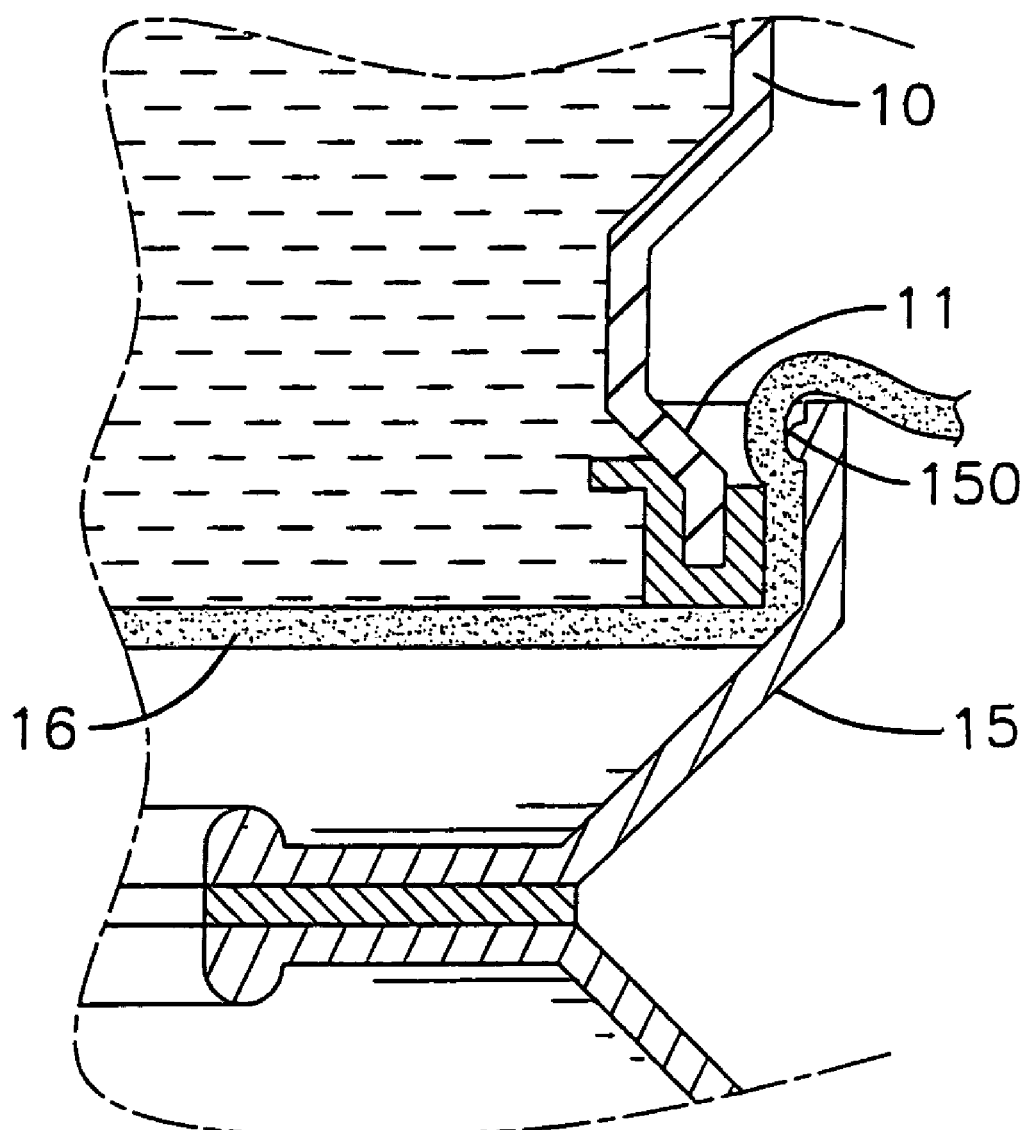
FIG. 2 is a partial enlarged schematic view showing the connection of the examining device

With reference to FIG. 2 and using FIG. 1 for reference, it is noted that the connector (15) is a ring-like member and has an upper ring (15a) with a first annular projection (151) formed on an inner face of the upper ring (15a) to correspond to the first groove (11) of the first container (10) and a lower ring (15b) with a second annular projection (152) formed on an inner face of the lower ring (15b) to correspond to the second groove (13) of the second container (12).

Figure 3:
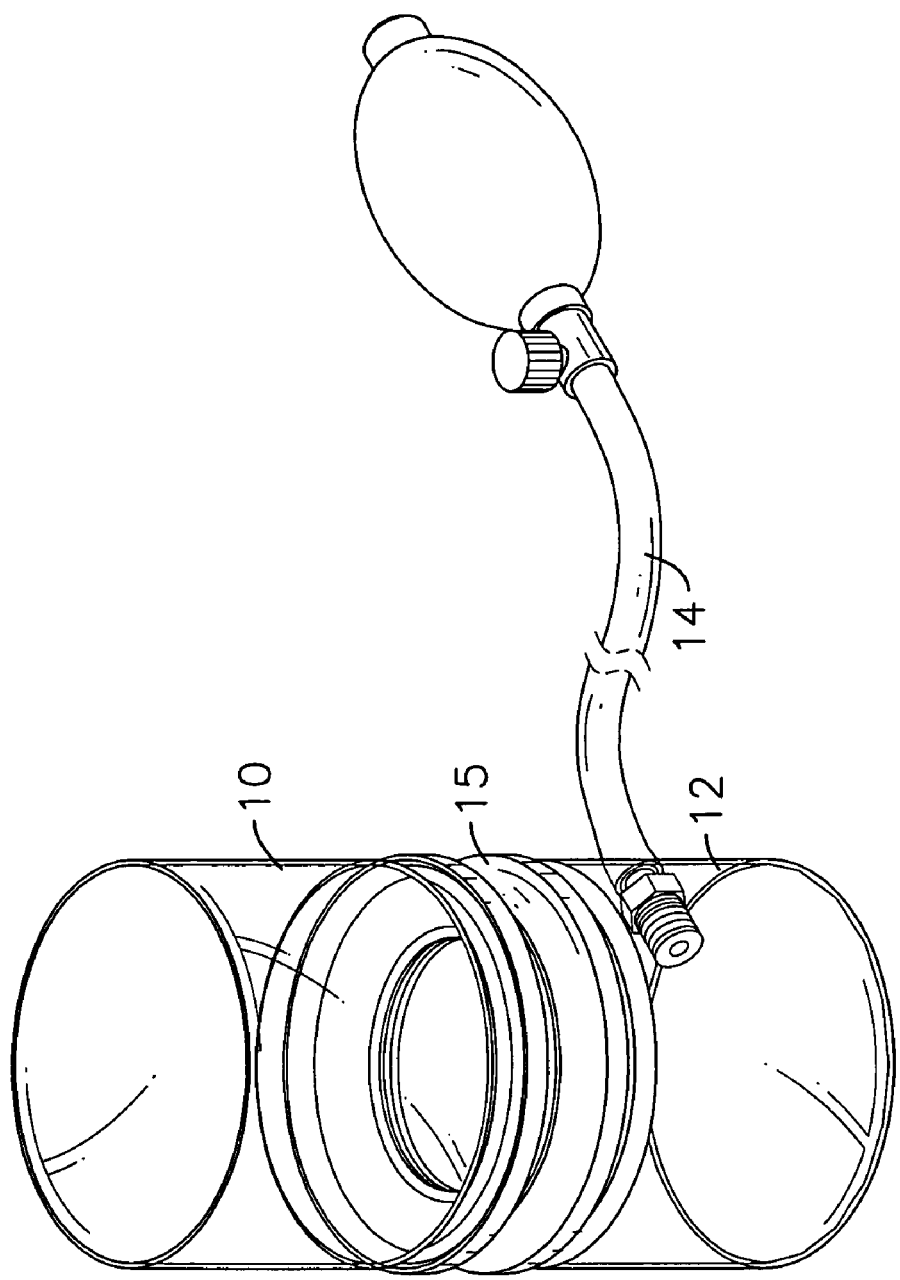
FIG. 3 is a perspective view showing the assembled examining device of the present invention.

With reference to FIG. 3, when the examining device is assembled, it is to be noted that the nozzle (143) is securely connected to the air hole (120) of the second container (12). The second annular projection (152) is received in the second groove (13) of the second container (12) and the first annular projection (151) is received in the first groove (11) of the first container (10).

Figure 4:
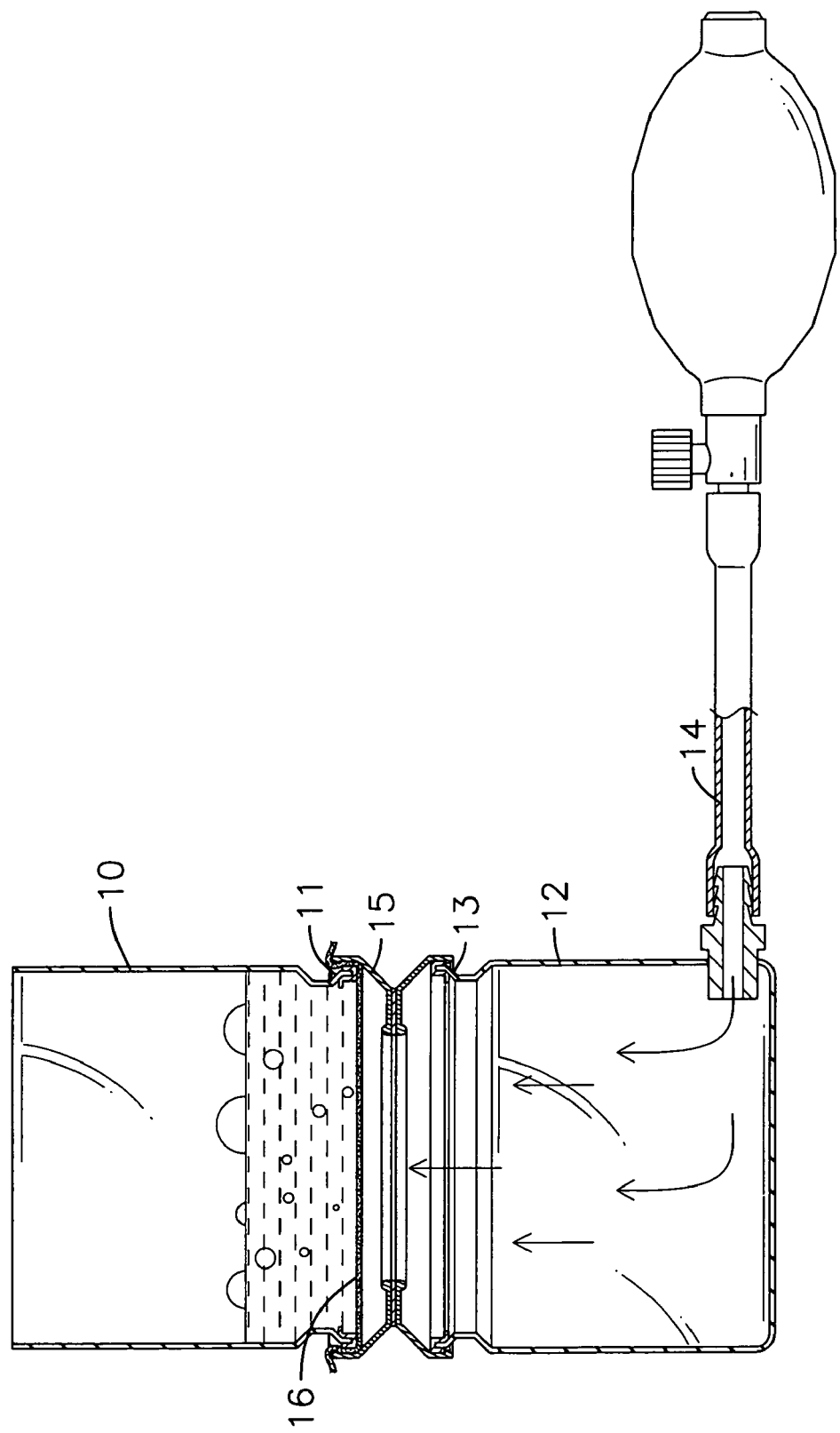
FIG. 4 is a schematic cross sectional view showing the application of the examining device.

With reference to FIG. 4, when the examining device of the present invention is in application with a cloth (16), the cloth (16) is placed on top of the connector (15). Then, after the first container (10) is placed on top of the connector (15) and the first annular projection (151) is received in the first groove (11) of the first container (10), the cloth (16) is securely clamped by an inner face defining the first groove (11) and the first annular projection (151) of the connector (15). When the aforementioned assembly is completed, the first container (10) is filled with water from the top open end of the first container (10) and air is pumped into the second container (12) by an operator squeezing the air bulb (241). Therefore, the user is able to observe whether the cloth (16) is water resistant and ventilatory by observing whether water passes down into the second container (12) and air passes up into the first container (10).

Figure 5:
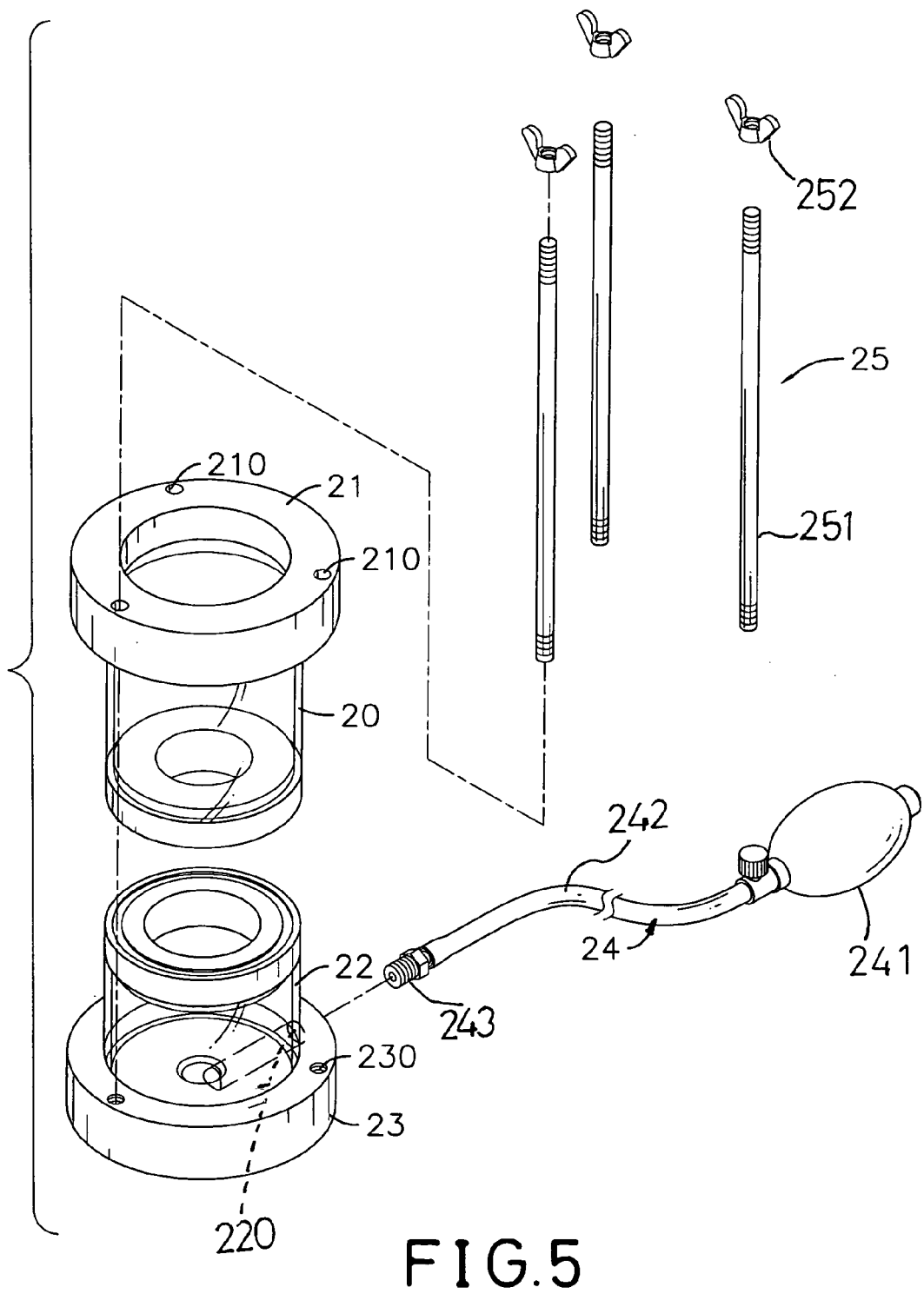
FIG. 5 is an exploded perspective view showing a different embodiment of the examining device of the present invention.

With reference to FIG. 5, a different embodiment of the present invention is shown and has a first container (20), a second container (22), an air supply device (24) and a securing device (25).

The first container (20) has two open ends with a top ring (21) formed on a peripheral top edge of the first container (20) and having multiple through holes (210) defined through the top ring (21). The second container (22) has an open end formed on a top of the second container (22) and a closed end formed on a bottom of the second container (22) and having a bottom ring (23) formed on a peripheral bottom edge of the second container (22) and having multiple threaded holes (230) defined through the bottom ring (23) to correspond to and align with the through holes (210) of the top ring (21). An air hole (220) is defined through a side wall of the second container (22) to allow the surrounding air to communicate with the inside of the second container (22).

The air supply device (24) includes an air bulb (241), a tube (242) extending out from the air bulb (241) and a nozzle (243) formed on a free end of the tube (242) to correspond to the air hole (220) of the second container (22).

The securing device (25) has multiple threaded bolts (251) and nuts (252) to correspond to the through holes (210) of the first container and the threaded holes (230) of the second container (22).

Figure 6:
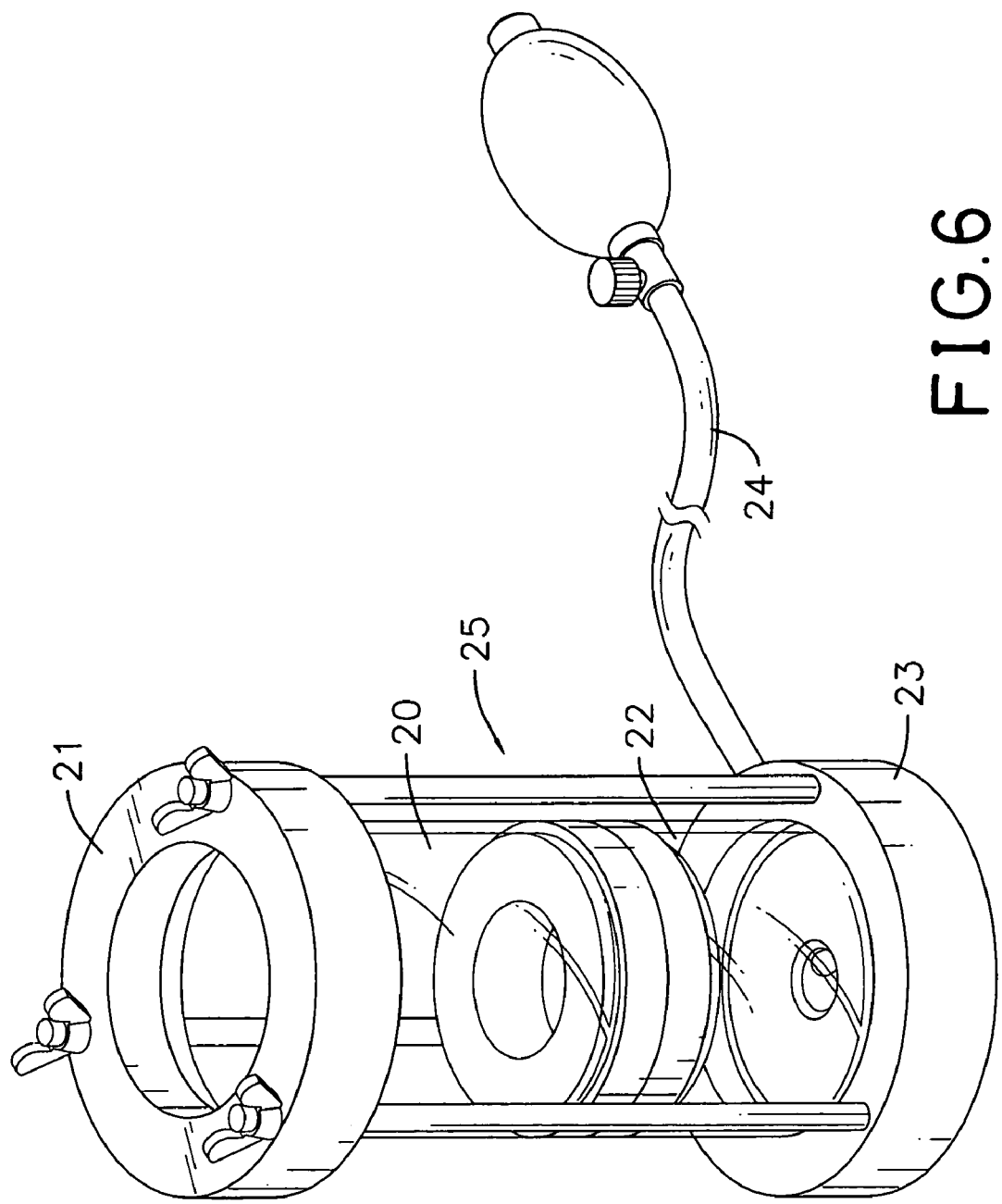
FIG. 6 is a perspective view showing the assembled examining device of the present invention.

With reference to FIG. 6, it is noted that after the examining device of the present invention is assembled, the threaded bolts (251) are extended through the through holes (210) and into the threaded holes (230) to combine the first and the second containers (21,22). The nuts (252) are applied to screw onto the threaded bolts (251) so as to securely engage the first container (21) with the second container (22). The nozzle (243) is connected to the air hole (220) of the second container (22).

Figure 7:
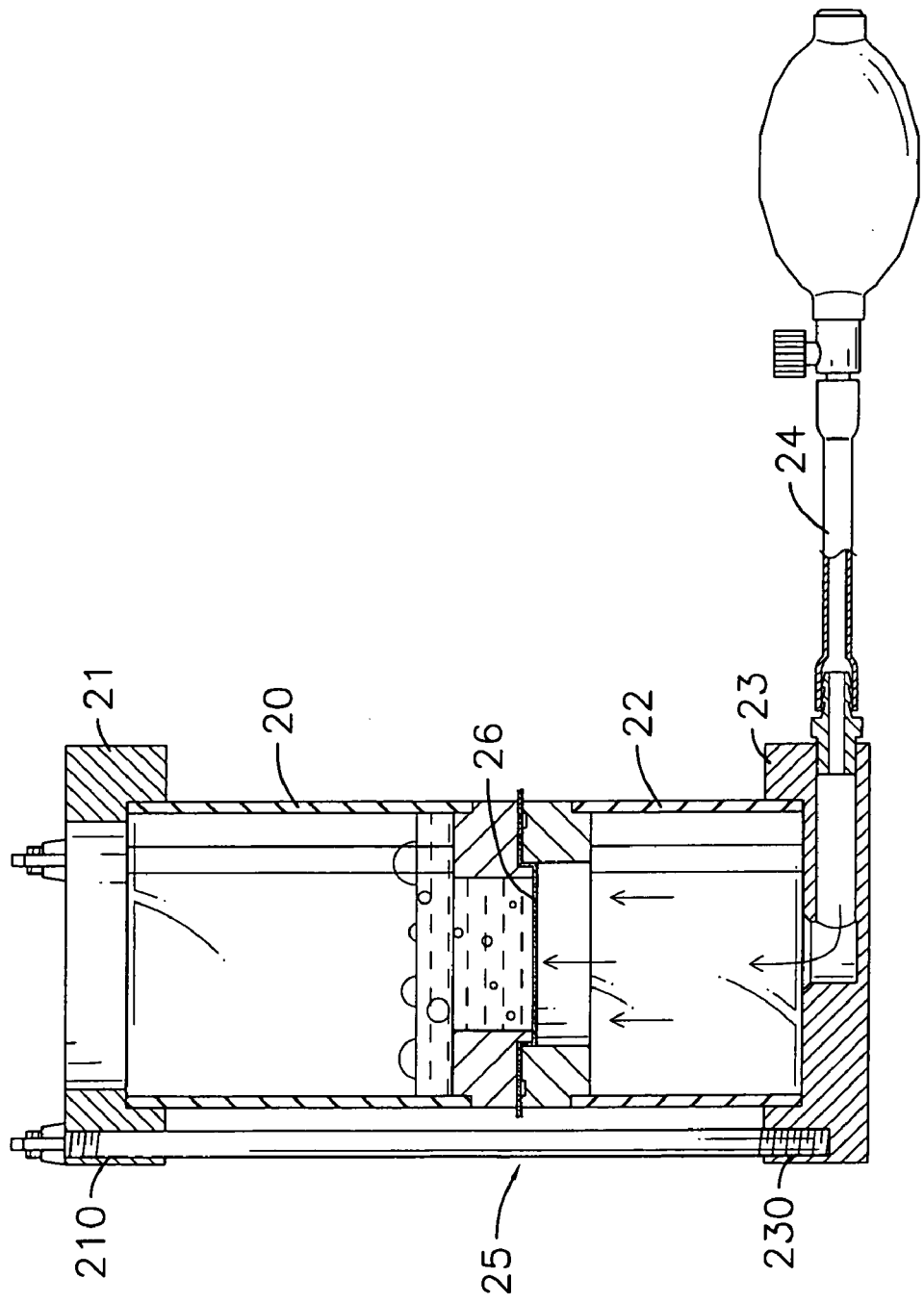
FIG. 7 is a schematic cross sectional view showing the application of the examining device of the present invention.

With reference to FIG. 7, before the application of the examining device, a cloth (26) is first sandwiched between the bottom of the first container (20) and the top of the second container (22). After the extension of the threaded bolts (251) into the through holes (210) and the threaded holes (230) and the nuts (252) are screwed onto the threaded bolts (251), the secure engagement between the first container (20) and the second container (22) securely clamps the cloth (26). Thus by pouring water into the first container (20) from the top open end of the first container (20), an operator is able to observe whether the cloth (26) is water resistant by whether water passes through the cloth. In the meantime, pumping air into the second container (22) by the operator squeezing the air bulb (241) to cause air to pass into the second container (22) via the nozzle (243) reveals whether bubbles pass through the cloth (26) and into the water in the first container (20). If bubbles do pass through the cloth (26), the cloth (26) is ventilatory.

It is to be noted that the entire structure of the examining device is simple and thus the cost is low. Further the testing procedure is quite easy for the operator so that the test can be performed any time at any place.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A water resistant and ventilatory examining device for cloth comprising:
   a first container (10) having two opposite open ends;
   a second container (12) having a closed end and an open end;
   means for combining the first container (10) and the second container (12), wherein the combining means is a ring-like member and has an upper ring formed on a top periphery of the member and a lower formed on a bottom periphery of the member such that the upper ring and the bottom ring are able to respectively engage with a bottom periphery of the first container and a top periphery of the second container in a watertight manner; and,
   an air supply device (14) in connection with the second container (12) to supply air into the second container, whereby after a cloth is sandwiched between the combining means and the first container (10), the first container (10) is filled with water and the second container (12) is supplied with air such that observation made to see if water seeps through the cloth and air passes through the cloth is able to test capabilities of the cloth.

2. The examining device as claimed in claim 1, wherein the air supply device (14) includes an air bulb (141), a tube (142) extending out of the air bulb (141) and a nozzle (143) formed on a free end of the tube (142) to engage with an air hole (120) defined in a side wall of the second container (12) such that squeezing the air bulb (141) is able to pump air into the second container (12).

3. The examining device as claimed in claim 1, wherein the upper ring (15a) has a first annular projection (151) and the lower ring has a second annular projection (152) to respectively engage with the bottom periphery of the first container (10) and the top periphery of the second container (12) in a watertight manner.

4. The examining device as claimed in claim 3, wherein the air supply device (14) includes an air bulb (141), a tube (142) extending out of the air bulb (141) and a nozzle (143) formed on a free end of the tube (142) to engage with an air hole (120) defined in a side wall of the second container (12) such that squeezing the air bulb (141) is able to pump air into the second container (12).

5. The examining device as claimed in claim 3, wherein the first container (10) has a first groove (11) defined in an outer periphery of the first container (10) to receive therein the first annular projection (151) and the second container (12) has a second groove (13) define in an outer periphery of the second container (12) to receive therein the second annular projection (152).

6. The examining device as claimed in claim 5, wherein the air supply device (14) includes an air bulb (141), a tube (142) extending out of the air bulb (141) and a nozzle (143) formed on a free end of the tube (142) to engage with an air hole (120) defined in a side wall of the second container (12) such that squeezing the air bulb (141) is able to pump air into the second container (12).

7. A water resistant and ventilatory examining device for cloth comprising:
   a first container having two opposite open ends;
   a second container having a closed end and an open end;
   means for combining the first container and the second container, and,
   an air supply device in connection with the second container to supply air into the second container,
   whereby after a cloth is sandwiched between the combining means and the first container, the first container is filled with water and the second container is supplied with air such that observation made to see if water seeps through the cloth and air passes through the cloth is able to test capabilities of the cloth, wherein the combining means has a top ring (21) formed on a top periphery of the first container (20) and having a plurality of through holes (210) defined through the top ring (21), a bottom ring (23) formed on a bottom periphery of the second container (22) and having a plurality of threaded holes (230) corresponding to the through holes (210) of the top ring (21), a plurality of threaded bolts (251) extending through the through holes (210) and screwingly received into the threaded holes (230) and a plurality of nuts (252) engaging with the respective threaded bolts (251) to secure engagement between the first container (20) and the second container (22).

8. The examining device as recited in claim 7, wherein the air supply comprises an air bulb, a tube connected to and extending out of the air bulb, and a nozzle formed on a free end of the tube to engage with an air hole defined in a side wall of the second container such that squeezing the air bulb causes air to be pumped into the second container.

* * * * *